US012765825B2

(12) United States Patent
Weiser et al.

(10) Patent No.: US 12,765,825 B2
(45) Date of Patent: Oct. 20, 2026

(54) COMPOSITE COMPONENT COMPRISING A PIECE OF MATERIAL COMPOSED OF FOAM MATERIAL OR ELASTOMER MATERIAL

(71) Applicants: INNOME GMBH, Espelkamp (DE); COVESTRO DEUTSCHLAND AG, Leverkusen (DE)

(72) Inventors: Marc-Stephan Weiser, Kürten (DE); Martin Hüttner, Leverkusen (DE); Klas-Moritz Kossel, Verden (DE); Marco Ahlswede, Bad Fallingbostel (DE); Thorsten Krämer, Langenfeld (DE); Daniel Baasner, Minden (DE); Bjarne Muth, Lübbecke (DE); Eike Wilhelm Kottkamp, Lübbecke (DE)

(73) Assignees: Innome GmbH, Espelkamp (DE); Deutschland AG, Leverkusen (DE)

( * ) Notice: Subject to any disclaimer, the term of this patent is extended or adjusted under 35 U.S.C. 154(b) by 523 days.

(21) Appl. No.: 18/257,984

(22) PCT Filed: Dec. 17, 2021

(86) PCT No.: PCT/EP2021/086388
§ 371 (c)(1),
(2) Date: Jun. 16, 2023

(87) PCT Pub. No.: WO2022/129464
PCT Pub. Date: Jun. 23, 2022

(65) Prior Publication Data

US 2024/0050011 A1 Feb. 15, 2024

(30) Foreign Application Priority Data

Dec. 18, 2020 (EP) .................................... 20215564

(51) Int. Cl.
*A61B 5/263* (2021.01)
*A61B 5/00* (2006.01)
(Continued)

(52) U.S. Cl.
CPC ............ *A61B 5/263* (2021.01); *A61B 5/6801* (2013.01); *B32B 5/18* (2013.01); *B32B 7/12* (2013.01);
(Continued)

(58) Field of Classification Search
CPC . A61B 5/263; A61B 5/6801; A61B 2562/164; B32B 5/18; B32B 7/12;
(Continued)

(56) References Cited

U.S. PATENT DOCUMENTS 3,882,853 A * 5/1975 Gofman ................ A61B 5/265 600/397
2009/0292194 A1 11/2009 Libbus
(Continued)

FOREIGN PATENT DOCUMENTS

EP 2384785 A2 11/2011
WO 2008057884 A2 5/2008
(Continued)

OTHER PUBLICATIONS

European Patent Office, Mitteilung (communication in a corresponding application), May 17, 2021.
(Continued)

*Primary Examiner* — Lindsey G Wehrheim
(74) *Attorney, Agent, or Firm* — Laurence P. Colton; Smith Tempel Blaha LLC

(57) ABSTRACT

A composite component having a piece of material which is elastic in particular and is composed of a foam material or an elastomer material or a silicone, where the piece of material is bonded, inextricably in particular, to a film sensor
(Continued)

for measurement of one or more parameters, especially parameters of a human or animal body, having a piece of film with at least one electrical wire disposed on said piece of film, and having at least one measurement sensor which is preferably disposed on said piece of film and is connected to the electrical wire in an electrically conductive manner.

20 Claims, 11 Drawing Sheets

(51) Int. Cl.

| | |
|---|---|
| ***B32B 5/18*** | (2006.01) |
| ***B32B 7/12*** | (2006.01) |
| ***B32B 27/06*** | (2006.01) |
| ***B32B 27/08*** | (2006.01) |
| ***B32B 27/32*** | (2006.01) |
| ***B32B 27/40*** | (2006.01) |

(52) U.S. Cl.
CPC ............ *B32B 27/065* (2013.01); *B32B 27/08* (2013.01); *B32B 27/32* (2013.01); *B32B 27/40* (2013.01); *A61B 2562/164* (2013.01); *B32B 2266/0278* (2013.01); *B32B 2274/00* (2013.01); *B32B 2307/72* (2013.01); *B32B 2307/7246* (2013.01); *B32B 2457/00* (2013.01); *B32B 2535/00* (2013.01)

(58) Field of Classification Search
CPC ....... B32B 27/065; B32B 27/08; B32B 27/32; B32B 27/40; B32B 2266/0278; B32B 2274/00; B32B 2307/72; B32B 2307/7246; B32B 2457/00; B32B 2535/00
See application file for complete search history.

(56) References Cited

U.S. PATENT DOCUMENTS

| | | | |
|---|---|---|---|
| 2011/0021889 | A1 | 1/2011 | Hoss |
| 2012/0088999 | A1 | 4/2012 | Bishay |
| 2017/0223846 | A1 | 8/2017 | Elolampi |

FOREIGN PATENT DOCUMENTS

| | | | | | |
|---|---|---|---|---|---|
| WO | 2015184391 | A1 | | 12/2015 | |
| WO | 2016081075 | A1 | | 5/2016 | |
| WO | 2016164623 | A1 | | 10/2016 | |
| WO | WO-2019236993 | A1 | * | 12/2019 | ........... A61B 5/6833 |

OTHER PUBLICATIONS

WIPO, International Search Report (in a corresponding application), Mar. 14, 2022.
European Patent Office, Mitteilung (communication in a related application), Jul. 2, 2021.
WIPO, International Search Report (in a related application), Apr. 4, 2022.

* cited by examiner

COMPOSITE COMPONENT COMPRISING A PIECE OF MATERIAL COMPOSED OF FOAM MATERIAL OR ELASTOMER MATERIAL

CROSS REFERENCE TO RELATED APPLICATIONS

This application is the US national phase of and claims the benefit of and priority on International Application No. PCT/EP2021/086388 having an international filing date of 17 Dec. 2021, which claims priority on and the benefit of European Patent Application No. 202155644.4 having a filing date of 18 Dec. 2020.

BACKGROUND OF THE INVENTION

Technical Field

The present invention relates to a composite component comprising a piece of material composed of a foam material or an elastomer material or a silicone, and having (at least) one measurement sensor for detection of one or more parameters, especially parameters of a human or animal body, and to a sensor unit comprising such a composite component.

Prior Art

There exist various sensor units with measurement sensors on the market. Among the sensor units known in the medical sector, for example, are those that are secured to the human or animal body and which can be used to detect various body parameters, for instance the electrical activity of the heart or brain. In general, these sensor units—as well as one or more suitable measurement sensors—have an electronics unit comprising an energy supply, with which the respective measurement sensor is operated and which can store and/or evaluate and/or pass on the measurement results.

The known sensor units generally have significant bulk, since the electronics unit, for protection from environmental influences, has to be/is housed in a rigid plastic container. Not only is this disruptive, but it is especially so in the abovementioned use of such sensor units in the medical sector, since they can for example be perceived there as objectionable by the respective person on whose body the sensor unit is secured.

There is a need to make sensor units firstly thinner and less bulky, and secondly less rigid, such that they are perceived as less objectionable, for example in the abovementioned end use.

BRIEF SUMMARY OF THE INVENTION

In the light of that, it is an object of the present invention to specify a component having a measurement sensor that can be part of a sensor unit and enables the sensor unit to be comparatively thin and/or comparatively pliable.

This object is achieved by a composite component comprising a piece of material which is elastic in particular and is composed of a foam material or an elastomer material or a silicone, where the piece of material is bonded, inextricably in particular, to a film sensor for measurement of one or more parameters, especially parameters of a human or animal body, having a piece of film with at least one electrical wire disposed on said piece of film, and having at least one measurement sensor which is disposed on said piece of film and is connected to the electrical wire in an electrically conductive manner, or of embodiment 1; and by a sensor unit comprising such a composite component comprising an electronics portion which is connectable, especially releasably, to the composite component and includes an electronics unit for operating the film sensor of the composite component, or of embodiment 20.

Correspondingly, a composite component of the invention comprises a piece of material composed of a foam material or an elastomer material or a silicone, where the piece of material is bonded, inextricably in particular, to a film sensor for measurement of one or more parameters, especially parameters of a human or animal body, having a piece of film with at least one electrical wire disposed on said piece of film, and having at least one measurement sensor which is preferably disposed on said piece of film and is connected to the electrical wire in an electrically conductive manner.

Such a composite component, through the use of a film sensor which is inherently flat or thin, enables integration into a sensor unit as sensor portion or use as a constituent of such a sensor unit such that the sensor unit takes on a particularly flat construction. This may, for example, be a sensor unit for securing to a human or animal body, especially to the skin of the body, with which one or more body parameters can be measured. The utilization specifically of the piece of material made of foam material or elastomer material or silicone as carrier material for the film sensor is particularly advantageous. This is because, among other reasons, this foam material is producible in virtually any shape in a cost-effective manner, is simultaneously of comparatively low weight and additionally—according to the material—can optionally be designed so as to be flexible, which can not least ensure good comfort when wearing a sensor unit produced therewith. Ultimately, it is advantageously possible to make use of the fact that foam material in particular, for example, can generally absorb (unwanted) liquids, for example body fluids etc.

With regard to the connection of the film sensor to the piece of material, the piece of film of the film sensor may be bonded to the piece of material, especially cohesively, inextricably or firmly. The bond is especially to an outer face thereof. The bond may, for example, be made by adhesive bonding, more preferably by means of a double-sidedly adhesive piece of adhesive material. Alternatively, the piece of film could also be laminated onto the piece of material. Various bonding variants are conceivable here.

The material for the piece of material may, for example, be any material that the person skilled in the art would use for buffering of impacts. The elastic piece of material is preferably composed of a material of low to zero cytotoxicity. The material is preferably selected from the group consisting of a gel, a hydrogel, a foam, or a combination of the two.

The material is preferably a thermoplastically formable foam. The foam material is preferably selected from the group consisting of a silicone, a polystyrene (PS), a polypropylene (PP), a polyvinylchloride (PVC), a polyurethane (PU), a thermoplastic polyurethane (TPU), a chloroprene, a natural rubber, an acrylonitrile-butadiene rubber or a combination of at least two of these. The foam material preferably includes a thermoplastic polyurethane.

The foam material has preferably been produced by mixing a first polyurethane dispersion (A) with at least a second polyurethane dispersion (B), optionally with addition of further additives, foaming and subsequent drying of the mixture, where the polyurethane dispersion (A) is obtainable by preparing A) isocyanate-functional prepolymers from
   A1) organic polyisocyanates
   A2) polymeric polyols having number-average molecular weights of 400 to 8000 g/mol, preferably 400 to 6000 g/mol, or preferably from 600 to 3000 g/mol, and OH functionalities of 1.5 to 6, preferably 1.8 to 3, or preferably from 1.9 to 2.1, and
   A3) optionally hydroxy-functional compounds having molecular weights of 62 to 399 g/mol, and
   A4) optionally isocyanate-reactive, anionic or potentially anionic and optionally nonionic hydrophilizing agents, and
B) then wholly or partly reacting the free NCO groups thereof
   B1) optionally with amino-functional compounds having molecular weights of 32 to 400 g/mol and
   B2) with amino-functional, anionic or potentially anionic hydrophilizing agents with chain extension, and dispersing the prepolymers in water before, during or after step B), with conversion of any potentially anionic groups present to the anionic form by partial or complete reaction with a neutralizing agent, and wherein the second polyurethane dispersion (B) is obtainable by reactive conversion of at least the following components:

A. an aliphatic polyisocyanate component having an average isocyanate functionality of ≥1.8 and ≤2.6,
B. a polymeric polyether polyol component;
C. an amino-functional chain extender component having at least 2 isocyanate-reactive amino groups, containing at least one amino-functional compound C1. that has no ionic or ionogenic groups, and/or an amino-functional compound C2. that has ionic or ionogenic groups,
D. optionally further hydrophilizing components other than C2.,
E. optionally hydroxy-functional compounds having a molecular weight of 62 to 399 mol/g,
F. optionally further polymeric polyols other than B.,
G. a compound that has exactly one isocyanate-reactive compound, or a compound that has more than one isocyanate-reactive group, where only one of the isocyanate-reactive group reacts under the reaction conditions chosen with the isocyanate groups present in the reaction mixture, and
H. optionally an aliphatic polyisocyanate component having an average isocyanate functionality of >2.6 and ≤4, where components B. and F. together contain ≤30% by weight of component F., preferably ≤20% by weight of component F., or preferably ≤10% by weight of component F., based on the total mass of components B. and F.

Examples of the production, possible compositions and properties of the foamed article, referred to here as foam material, that arises from the reactive conversion of the first polyurethane dispersion (A) produced from the prepolymer A) composed of components A1) to A4), and B1), B2), with the second polyurethane dispersion (B) composed of components A. to H. can be found in publication WO 2020/173760, especially pages 2 to 23.

If securing of the composite part to a body is intended, for example when it is a constituent of the abovementioned sensor unit, or securing of the sensor unit to the body, the composite part or sensor unit may preferably be adhesive bonded to the skin of the body. In particular, the film sensor, preferably the piece of film of the film sensor (at least a portion thereof in each case), may be adhesive bonded to the skin.

The material used for the adhesive bonding of the composite part or film sensor, especially of the piece of film, to the skin of the body may be any material that the person skilled in the art would select for the purpose. The material for adhesive bonding preferably comprises or takes the form of a non-cytotoxic adhesive. The adhesive is preferably selected from the group consisting of acrylic adhesive, a (thermoplastic) polyurethane adhesive, an epoxy resin adhesive, a silicone adhesive, a rubber adhesive, or a mixture of at least two of these. Preference is given to using one of the polyurethane adhesives as described in the publications of EP 3 502 156 A1 or US 2019/0233691 A1.

Other components of the composite component or sensor unit, for example of an electronics portion having an electronics unit for operating the film sensor, can also be adhesive bonded using the above-described adhesives. These may either be applied directly to the components or used as single- or double-sided adhesive tapes.

The foam material of the piece of material may be a polymer foam, especially a polyurethane foam.

In a preferred development of the invention, a first section of the piece of film of the film sensor may be disposed on and especially bonded (preferably inextricably) to a first side of the piece of material. A second section of the piece of film of the film sensor may be disposed on and especially bonded (preferably inextricably) to a second side of the piece of material which is especially parallel to the first side at least in one region.

It is preferable to use a flexible elastic film in or for the composite component, especially for or as the flexible piece of film. The film preferably includes a polymer selected from the group consisting of polyethylene, soft polyethylene (LDPE), polypropylene, polyethylene terephthalate, polybutylene terephthalate, polyurethane, thermoplastic polyurethane or a mixture or combination of at least two of these.

The film preferably has a permeability with respect to water vapor within a range from 2 to 100 g/24 h*m$^2$, preferably 3 to 50 g/24 h*m$^2$, more preferably 5 to 20 g/24 h*m$^2$ (determination in accordance with DIN 53122-1-2001 under conditions B (30° C. and 90% relative humidity), and was measured on 150 μm films, unless stipulated otherwise).

It is preferable to use the film, for example in the form of a membrane film, as water vapor barrier. The film, as well as low permeability for water and water vapor, should have a profile of mechanical properties that makes it suitable for use in a composite part or a sensor unit comprising such a composite part that can be subjected to mechanical stresses, for instance as a result of the movement of a person or animal on which the composite part or sensor unit may be secured. The film is preferably weldable, flexible under cold conditions, and stable to surfactants or other media influences, as occur in the daily life of a human or animal. The film should preferably be renderable or rendered antistatic.

The aforementioned properties of the film, especially of the membrane film, may preferably be achieved in that the film has a single- or multilayer structure, where preferably at least one layer includes consists of a thermoplastic polyurethane (TPU).

Preference is given in accordance with the invention to using TPUs, the longer-chain diol component of which is a polyester or polyether, and which has a Shore A hardness of preferably 75-95, more preferably 85-95, determined to DIN 53 505. Particular preference is given to TPUs with a polyether diol component (TPU ethers).

Preference is given to the combination of TPU ether and TPU ester layers in a multilayer film.

Suitable thermoplastic polyurethanes are obtainable, for example, under the following trade names: Desmopan® and Texin (Bayer MaterialScience AG, Leverkusen, DE), Elastollan® (Elastogran GmbH, Lemförde, DE), Estane® (Lubrizol Advanced Materials Inc., Cleveland, OH, USA) or Morthane® (Morton International, Inc., Chicago, Ill, USA).

The film preferably additionally includes, in at least one layer, especially in the layer formed from thermoplastic polyurethanes, commonly used additives selected from the group comprising I. antiblocking agents, inorganic or organic spacers, II. lubricants or demolding agents, Ill. pigments or fillers and IV. stabilizers or a combination of at least two of these.

The proportion of additives I to IV mentioned preferably adds up to between 0% by weight and 30% by weight.

The outer layer, especially the TPU layer, preferably contains up to 30% by weight of an antistat.

Additives present in the preferred films are described, for example, in Gächter and Müller in: Plastics Additives, Carl Hanser Verlag Munich, 4th edition (1996).

An at least three-layer construction of a multilayer film is preferably characterized in that at least one layer based on a polyethylene (PE), preferably a soft polyethylene, also called low-density polyethylene (LDPE), lies between two layers formed from thermoplastic polyurethane.

Suitable polyethylenes preferably have a density within a range from 0.915 to 0.935 g/I. The polyethylene preferably has an average molecular mass within a range from 5000 to 20 000 g/mol, further preferably within a range from 7000 to 15 000 g/mol.

Further preferably, the film has an at least five-layer structure, where TPU is present in the two outer layers. There is preferably a middle layer based on a polyethylene which is bonded to the two outer TPU layers via intermediate layers, called adhesion promoter layers, that are formed from a copolymer-based adhesion promoter.

Copolymer-based adhesion promoters are characterized by gradations both of polar and nonpolar molecular constituents. Particular preference is given to olefin-based polymer adhesion promoters.

The group of the olefin-based polymer adhesion promoters especially includes ethylene-vinyl acetate copolymers and ethylene-acrylate copolymers having a comonomer content lower than the olefin content. Particular preference is given to olefin-based copolymers having comonomer contents of 15% to 30% by weight.

Preference is given to films having a total thickness within a range from ≥50 to ≤1000 μm, further preferably from ≥70 to ≤900 μm, more preferably from ≥90 to ≤800 μm.

In the case of a multilayer film, the thickness of the individual layers of thermoplastic polyurethanes is preferably within a range from ≥20 to ≤350 μm, the thickness of the polyethylene layer within a range from ≥5 to ≤50 μm, and that of the adhesion promoter layers preferably within a range from ≥5 to ≤200 μm.

Preferably, the film consists of at least two outer layers of TPU and one inner layer of polyethylene, especially soft polyethylene.

Particularly suitable methods of producing the single- or multilayer film are the standard thermal forming methods for processing of plastics to give single- or multilayer sheetlike structures. One example here would be production by (co) extrusion, which is preferably effected by the blown film method. Because of the better composite adhesion achievable, coextrusion is preferred to a particular degree among the suitable production methods for multilayer thermoplastic sheet like structures.

The films described in the examples and comparative examples that follow were produced by blown film coextrusion. The screw tools used for digestion of thermoplastic resins are described in terms of their construction, for example, by Wortberg, Mahlke and Effen in: Kunststoffe, 84 (1994) 1131-1138, by Pearson in: Mechanics of Polymer Processing, Elsevier Publishers, New York, 1985, or by the company Davis-Standard in: Paper, Film & Foil Converter 64 (1990) p. 84-90. Tools for shaping the melt to films are elucidated, inter alia, by Michaeli in: Extrusions-Werkzeuge [Extrusion Tools], Hanser Verlag, Munich 1991.

With regard to the at least one electrical wire mounted on the piece of film of the composite part, this may be printed on, preferably as a conductor track, by means of known printing methods or by (other) thin-layer techniques for electronic circuits.

It is further conceivable that the (at least one) measurement sensor as well, for example an electrode, is applied to the piece of film by one of these techniques. It is also conceivable, by means of the printing or thin-layer techniques, to print, or to apply by means of the thin-layer techniques, one or more electronic (semiconductor) components that may be additionally required on the piece of film, for example resistors, transistors, capacitors or the like.

The printing can be effected inter alia by means of inkjet printers or screen printers using polymer-based "inks" known per se, which are enriched with electrically conductive particles. Additionally possible are processes of applying conductive "inks" or materials having membrane functions by a dispenser process.

It is also conceivable to apply the (at least one) electrical wire and/or the (at least one) measurement sensor and/or the further electronic (semiconductor) component(s) by means of 3D printers.

With regard to the abovementioned two sections of the piece of film, these may be connected to one another, especially in a one-piece manner, by a connecting section of the piece of film, which is guided from the first side to the second side of the piece of material to form a turnover region in which the connecting section is turned, especially by 180°, preferably in a u shape, about an edge of a preferably plate-shaped edge region of the piece of material.

The measurement sensor may be disposed on the second section of the piece of film of the film sensor.

With regard to the (at least one) electrical wire, this may preferably be applied to an outer face of the piece of film remote from the piece of material, especially by means of an additive printing method.

Moreover, an electrically insulating insulator material layer that covers the electrical wire on the outside may be disposed on the second side of the piece of material, especially with contact to this second side.

The insulator material layer may cover the whole second section of the piece of film except for the measurement sensor(s).

In a further embodiment of the invention, the piece of film, especially the first section of the piece of film disposed on the first side of the piece of material, may have one or more electrical contact elements for contacting of the film sensor. These contact elements would be usable, for example, to connect contact elements of an electronics portion or an electronics unit of an electronics portion when these are assembled to give a sensor unit.

In that case, it may advantageously be the case that the measurement sensor of the composite part is disposed on the second side of the piece of material, especially on the second section of the piece of film already mentioned above.

The film sensor, especially the second section of the piece of film of the film sensor which is disposed on the second side of the piece of material, may additionally have one or more such measurement sensors, specifically at least one temperature sensor and/or one conductivity sensor and/or one pressure sensor and/or one impedance sensor. With one or more of these or other sensors, a sensor unit including a composite component of the invention would be able to detect corresponding measurements, on the basis of which the body parameters to be detected are then determined.

It may further be the case that the piece of material has a passage opening that especially extends from the first side to the second side. Through this could extend, for example, the main viewing direction of an electrooptical detection device, preferably comprising an (electronic) camera, which is assigned to an electronics portion of a or the sensor unit and is disposed, for example, on a circuit board of the electronics unit of the electronics portion.

The passage opening could be covered by a transparent protective layer which is especially disposed on the first and/or second side, which could protect the camera, for example.

The second side of the piece of material may also have one or more elevations that protrude with respect to at least one other region, especially a flat region, of said second side, where the or each measurement sensor is disposed on such an elevation.

As already indicated above, the composite component may be designed overall and intended to interact with an electronics portion having an electronics unit for operating the film sensor to form a sensor unit, especially a sensor unit for securing on a human or animal body, especially on the skin of the body, and to be connected, especially in a releasable manner, to the electronics portion, especially with preferably releasable electrically conductive connection of the contact element(s) of the composite component to the electronics unit of the electronics portion.

In a further embodiment of the invention, the piece of material of the composite component can have a depression which has preferably been introduced by embossment and which is bounded by a base wall and by a side wall which is connected in a one-piece manner to said base wall and laterally surrounds the depression, especially a depression in which the electronics portion of the sensor unit can be disposed.

The depression may have been introduced into the first side of the piece of material, in which case the first section of the piece of film of the film sensor may be disposed on the (inner) face of the base wall of the depression that faces the depression.

With regard to the dimensions of the composite part, the composite part may preferably have a length and/or a width between 20 mm and 200 mm, more preferably between 30 mm and 100 mm. The (construction) height may preferably be between 4 mm and 20 mm, more preferably between 6 mm and 15 mm. The (outer) contour or (outer) shape, especially in terms of the footprint, may preferably be round, square or rectangular.

With regard to the dimensions of the abovementioned sensor unit, the sensor unit may preferably have a length and/or a width between 20 mm and 200 mm, more preferably between 30 mm and 100 mm. The (construction) height may preferably be between 4 mm and 30 mm, more preferably between 6 mm and 20 mm. The (outer) contour or (outer) shape, especially in terms of the footprint, may preferably be square or rectangular.

With regard to the dimensions of the electronics portion, the electronics portion may preferably have a length and/or a width between 20 mm and 80 mm, more preferably between 30 mm and 60 mm. The (construction) height may preferably be between 4 mm and 15 mm, more preferably between 6 mm and 12 mm. The (outer) contour or (outer) shape, especially in terms of the footprint, may preferably be round.

It will be apparent that the abovementioned (construction) height of the sensor unit means the dimension thereof which, when the sensor unit is secured as intended on the skin of the body, would determine the extent of the entire sensor unit perpendicularly or at least approximately perpendicularly to the skin surface.

The (construction) height of the composite part, where it is a constituent of such a sensor unit, or the height of the electronics portion means the respective corresponding dimension thereof in the same direction of extent as defined above, but solely based in each case on the sensor portion or electronics portion itself, i.e., if appropriate, in a state (possibly hypothetically) separated from the respective other component.

With regard, lastly, to the second section of the piece of film of the film sensor that has already been mentioned above, this may be disposed on an opposite side of the base wall from that side of the base wall facing the depression.

BRIEF DESCRIPTION OF THE DRAWINGS

Further features of the present invention will become apparent from the appended claims, from the description of preferred embodiments that follows, and from the appended drawings. The figures show:

DETAILED DESCRIPTION OF PREFERRED EMBODIMENTS

Figure 1A:
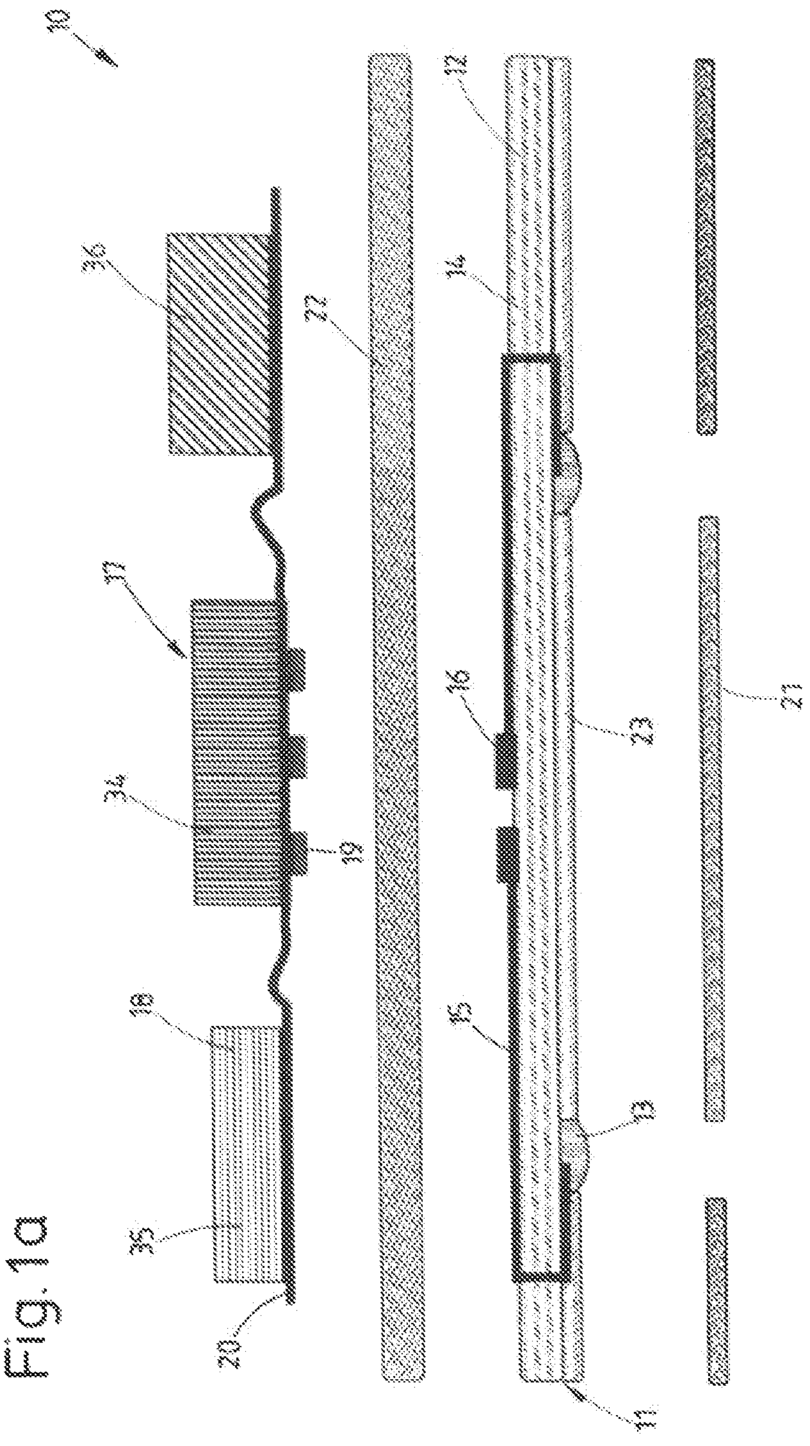
FIG. 1*a* a section diagram of a first embodiment of a sensor unit composed of the composite part of the invention and an electronics portion, in an (as yet) unbonded state of the individual parts that form the sensor unit, FIG. 1*b* the section diagram according to FIG. 1*a*, in a bonded or assembled state of the individual parts that form the sensor unit, FIG. 2*a* a section diagram of a second embodiment of a sensor unit composed of the composite part of the invention and an electronics portion, in an unbonded state of the individual parts that form the sensor unit, FIG. 2*b* the section diagram according to FIG. 2*a*, in a bonded state of the individual parts that form the sensor unit, FIG. 3*a* a section diagram of a third embodiment of a sensor unit composed of the composite part of the invention and an electronics portion, in an unbonded state of the individual parts that form the sensor unit, FIG. 3*b* the section diagram according to FIG. 3*a*, in a largely bonded state of the individual parts that form the sensor unit, FIG. 4*a* a section diagram of a fourth embodiment of a sensor unit composed of the composite part of the invention and an electronics portion, in an unbonded state of the individual parts that form the sensor unit, FIG. 4*b* the section diagram according to FIG. 4*a*, in a bonded state of the individual parts that form the sensor unit, FIG. 5*a* a section diagram of a fifth embodiment of a sensor unit composed of the composite part of the invention and an electronics portion, in an unbonded state of the individual parts that form the sensor unit, FIG. 5*b* the section diagram according to FIG. 5*a*, in a bonded state of the individual parts that form the sensor unit, FIG. 6 an exploded drawing of the fifth embodiment shown in FIGS. 5*a* and 5*b*.

There follows a description of an inventive sensor unit 10 comprising a sensor portion 11 and an electronics portion 17, wherein the sensor portion 11 takes the form of a composite part of the invention.

The sensor unit 10 shown in FIGS. 1*a*-5*b* is intended and designed to be secured to a human (or animal) body in order to detect body parameters. Such body parameters may, for example, be electrical activity of the heart or brain. The detection of various other body parameters is also naturally conceivable.

First of all, the components of such a sensor unit 10 that are possessed by all the embodiments shown in FIGS. 1*a*-5*b* are described hereinafter. Subsequently, the differences between the individual embodiments are addressed.

The sensor unit 10 of each embodiment comprises the sensor portion (or composite part) 11 with a film sensor 12 having a plurality of measurement sensors 13 in the present case (it will be apparent that one measurement sensor 13 may also be sufficient), and also an electronics portion 17 which is releasably connected to the sensor portion 11 in the present case and has an electronics unit 18 for operation of the film sensor 12.

The measurement sensors 13 are disposed on a flexible piece of film 14 (which serves as carrier for said measurement sensors 13) of the film sensor 12 of the sensor portion 11, specifically on a side of the piece of film 14 remote from the electronics portion 17.

The measurement sensors 13 are also connected in an electrically conductive manner by means of electrical wires 15 disposed on the piece of film 14 to (electrical) contact elements 16 that are likewise present on the piece of film 14 and serve for contacting of the film sensor 12.

The measurement sensors 13, the electrical wires 15 and/or the contact elements 16 may be applied to the piece of film 14, for example, by means of additive printing technology.

It will incidentally be apparent that it is also within the scope of the invention to dispose the measurement sensors 13 and/or the contact elements 16 outside the piece of film 14, for example directly adjacent thereto.

In general, the sensor unit 10 or the sensor portion 11 of the sensor unit 10 is secured on the skin of the person whose body parameters are to be detected in such a way that the measurement sensors 13 lie directly on the skin.

As shown explicitly (solely) by the embodiments of FIGS. 1*a*-3*b*, the sensor unit 10 can be secured here on the respective body, for example, by using flat, skin-compatible, double-sidedly adhesive pieces of adhesive material 21 (double-sided adhesive tape) which are correspondingly adhesively bonded by one side to the side of the sensor portion 11 that faces the body and by their other side to the skin of the respective body.

For electrical insulation, in addition, an insulation layer 23 is provided on the side of the piece of film 14 or of the film sensor 12 of the sensor portion 11 which is remote from the electronics portion 17, namely on the side facing the body in the case of use as intended, and this especially covers and electrically insulates the electrical wires 15 to the outside or toward the body.

With regard to the electronics unit 18 of the electronics portion 17, this has a measurement electronics unit 34 which is disposed on a circuit board 20 that is flexible in the present case, and to which the measurement sensors 13 of the sensor portion 11 are electrically connected and which receives and optionally evaluates the (measurement) signals from the measurement sensors 13.

A transmitter unit 35 designed as a radio module in the present case is additionally disposed on the circuit board 20 for wireless transmission of signals from the measurement sensors 13 or of information based thereon to a corresponding remote receiver unit (not shown).

The electronics unit 18 further comprises an energy or power supply 36, in the form of a battery in the present case, for the individual components of the electronics unit 18 or of the film sensor 12.

The aforementioned components are each disposed or secured on a first side of the circuit board 20 which is remote from the sensor portion 11.

On the opposite side of the circuit board 20 facing the sensor portion 11, this has electrical contact elements 19 that are connected in an electrically conductive manner to the electrical contact elements 16 of the film sensor 12.

For releasable securing of the electronics portion 17 to the sensor portion 11—similarly to the securing of the sensor unit 10 to the body of the user—(at least) one double-sided piece of adhesive material 22 is provided in the present case, which is (adhesive) bonded in contact with the contact elements 19 (as well) firstly to the side of the circuit board 20 facing the sensor portion, and secondly in contact with the contact elements 16 (as well) to the side of the piece of film 14 of the film sensor 12 that faces the circuit board 20 or the electronics portion 17.

The adhesive of the double-sided piece of adhesive material 22 is selected such that the electronics portion 17 is releasable from the sensor portion 11 if required. But an inextricable connection of these components is also within the scope of the present invention.

The double-sided piece of adhesive material 22 is in electrically conductive form, such that the electrically conductive connection between the contact elements 16 of the film sensor 12 and the contact elements 19 of the electronics unit 18 is brought about thereby.

The sensor unit 10 may, in accordance with the invention, likewise be of very flat construction overall by virtue of a/the flat construction of the electronics component 17 or have a low (construction) height. In the figures, the height of the sensor unit 10 corresponds to that dimension which determines the extent of the sensor unit 10 from the bottom upward, or in the present context the distance between the (outer) face of the sensor unit 10 or of the sensor portion 11 which is disposed on the body and the (outer) face of the sensor unit 10 or of the electronics portion 17 which is remote from the body.

Figure 1B:
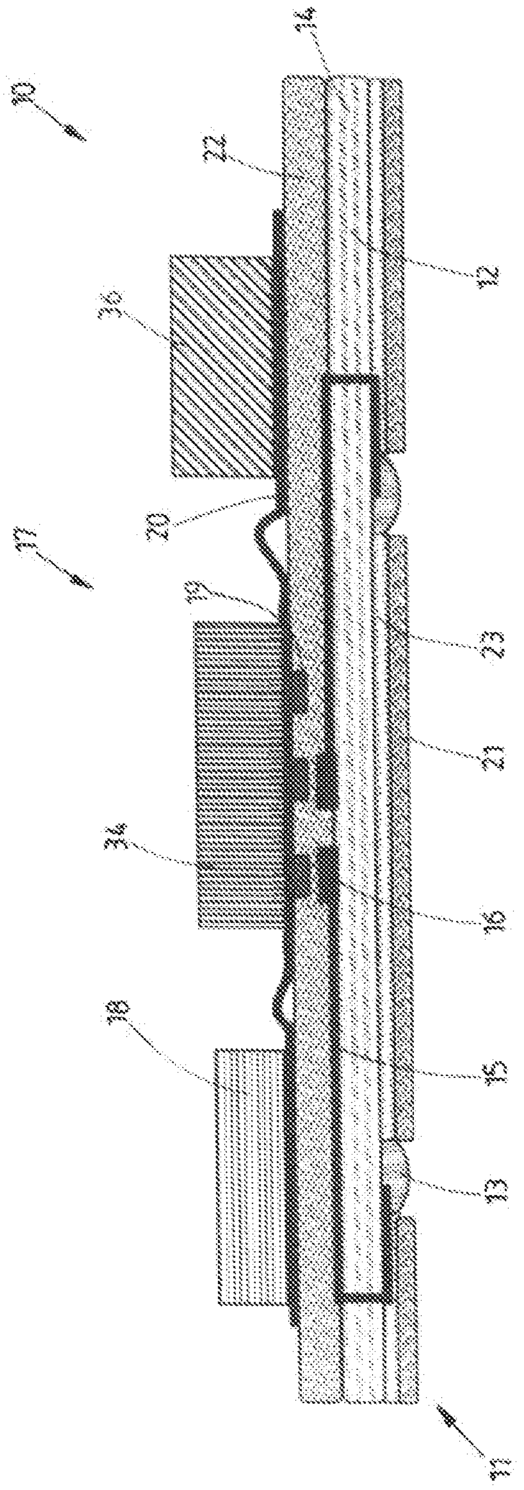

The embodiment of FIGS. 1*a*, 1*b* does not have any further components and/or peculiarities beyond the components described above.

Figure 2A:
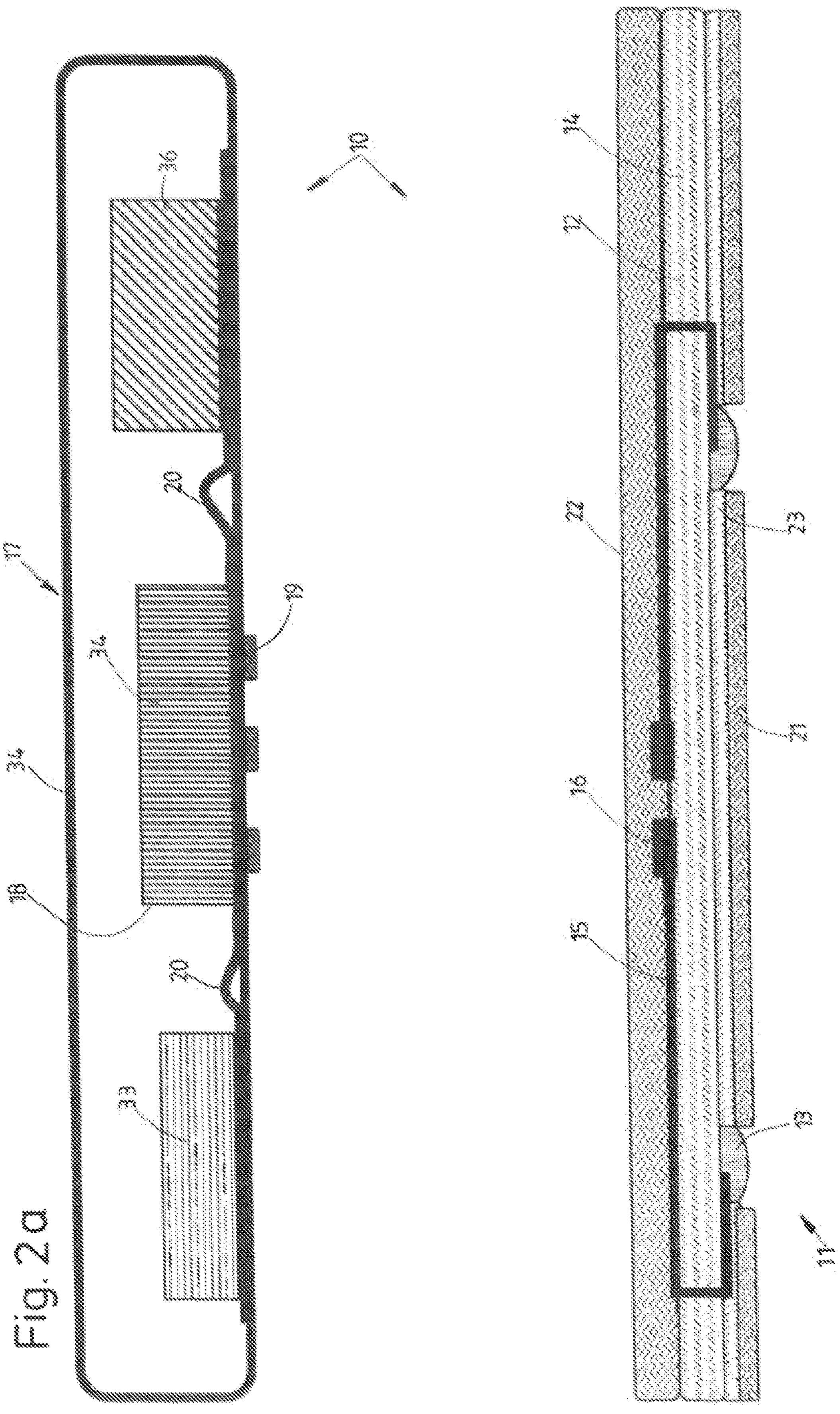
Figure 2B:
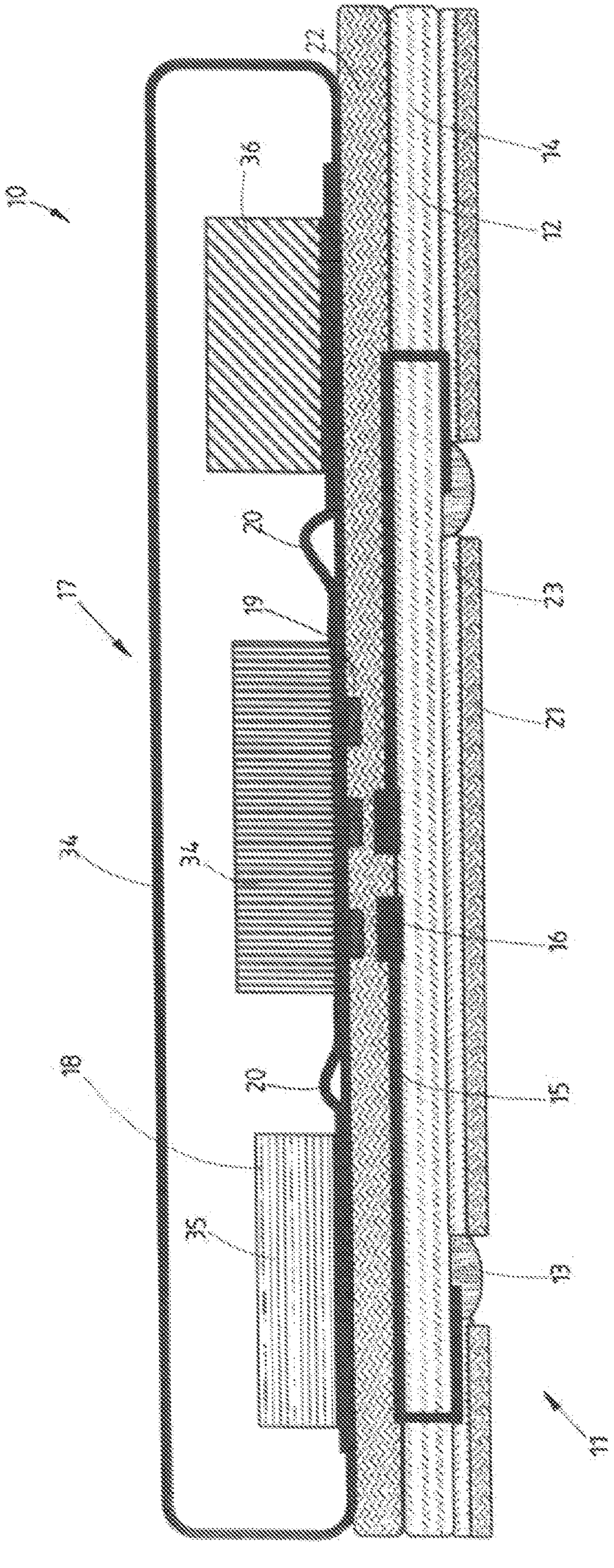

In the embodiment of FIGS. 2*a*, 2*b*, by contrast, the electronics portion 17 additionally has a protective casing 24 into which the electronics unit 18 is integrated and which surrounds the components of the electronics unit wholly or partly in a protective manner.

Figure 3A:
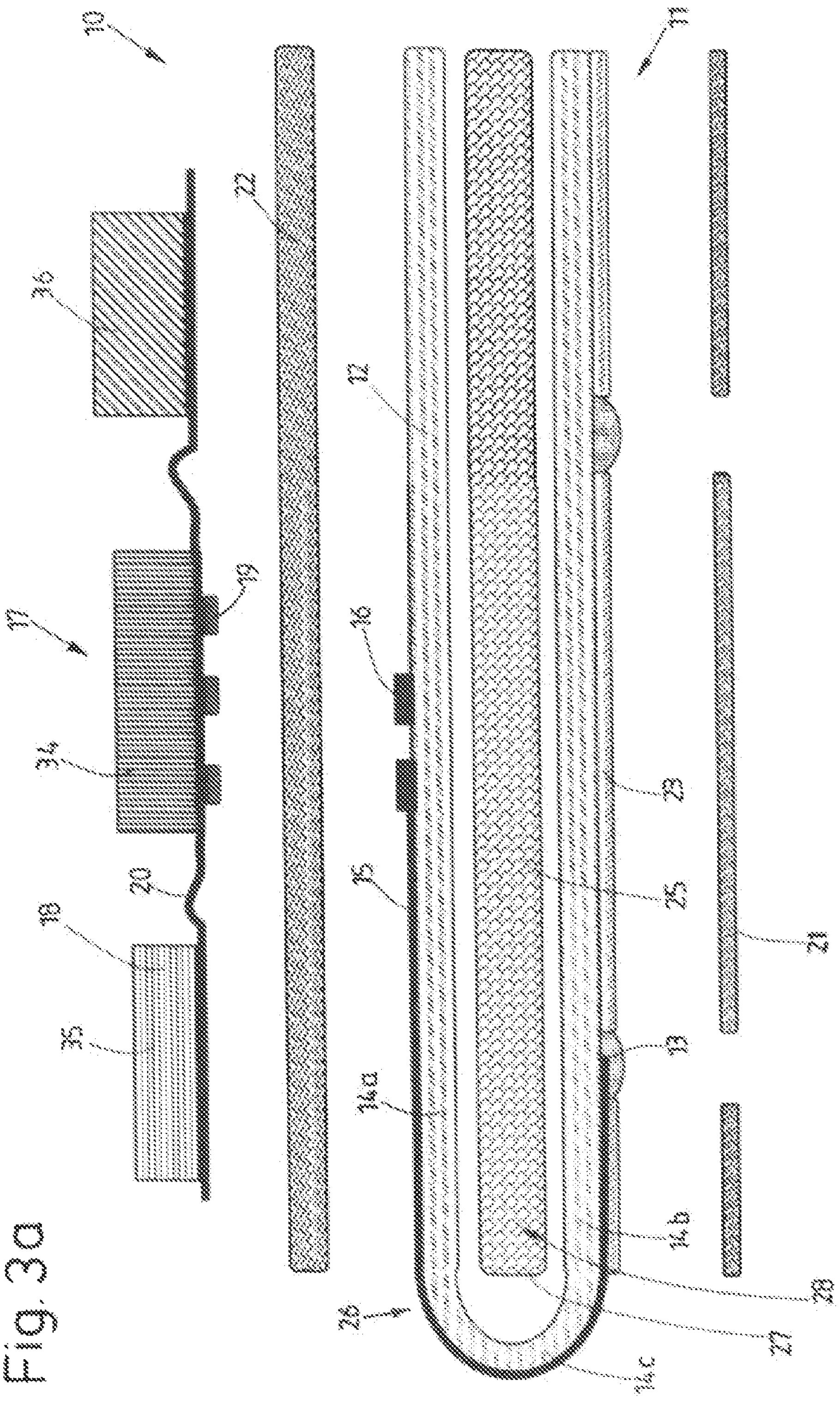
Figure 3B:
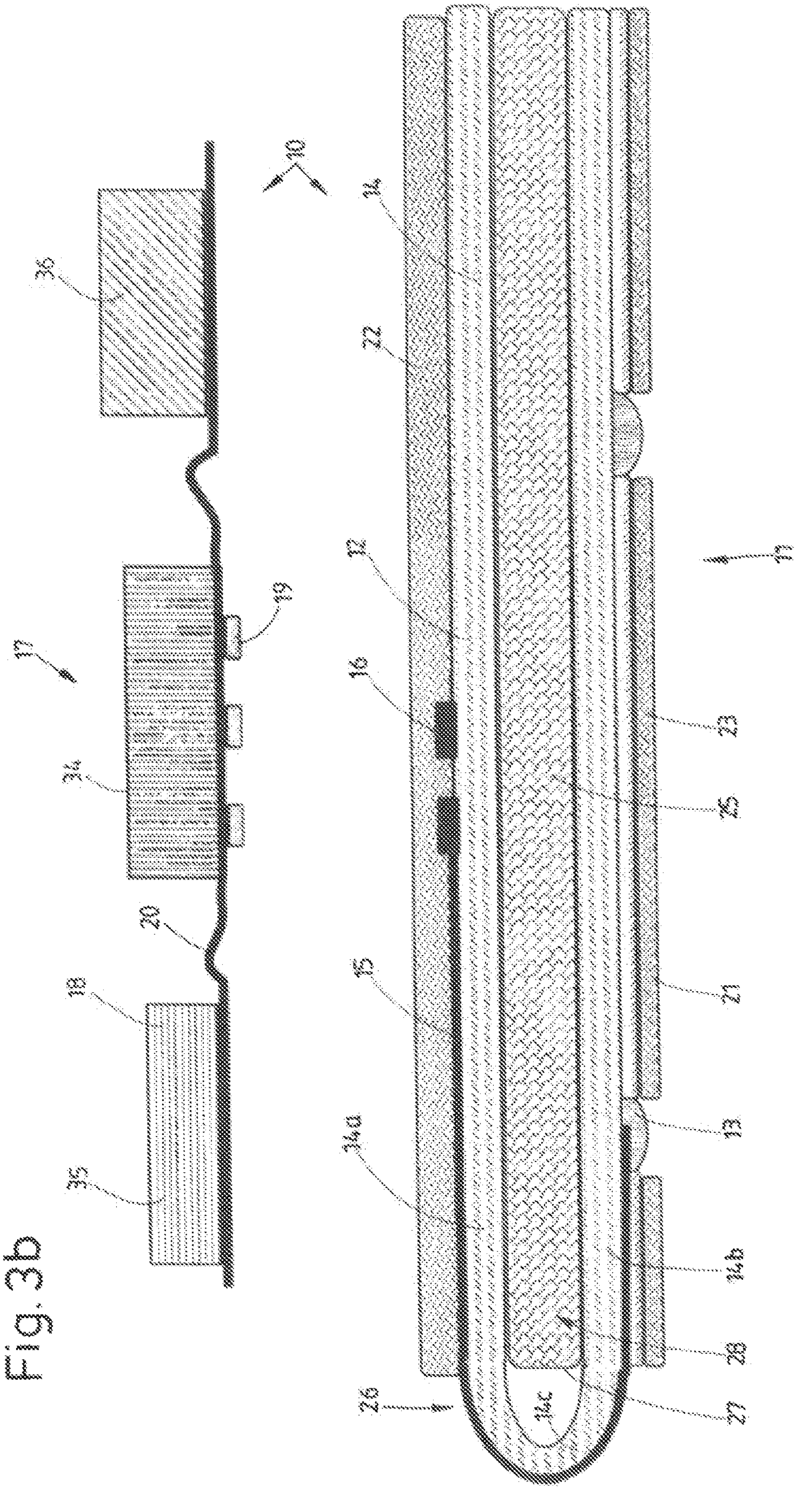

The embodiment of FIGS. 3*a*, 3*b* differs from the embodiment of FIGS. 1*a*, 1*b* in that the sensor portion 11 additionally includes a piece of material 25 made of polymer foam, for instance PU foam, to which the film sensor 12 is cohesively bonded, for example adhesive bonded, in the present context. It will be apparent that the invention also extends to various other modes of bonding between film sensor 12 and sensor portion 11.

As is apparent, a first section 14*a* of the piece of film 14 of the film sensor 12 is assigned to or disposed on a first side of the piece of material 25 of the sensor portion 11 that faces the electronics portion 17, and is fixedly bonded to that side.

A second section 14*b* of the piece of film 14 of the film sensor 12 is assigned or disposed on and fixedly bonded to a/the opposite second side of the piece of material 25 of the sensor portion 11 that faces the body.

The two sections 14*a*, 14*b* of the piece of film 14 are connected to one another in a one-piece manner by a connecting section 14*c* of the piece of film 14, so as to form a turnover region 26 in which the connecting section 14*c* is turned, in the present case by 180°, here roughly in a u shape, about an edge 27 of an edge region 28, which is platelet-shaped here, of the piece of material 25 of the sensor portion 11, and in this way is guided from the first side to the second side of the piece of material 25 of the sensor portion 11.

Alternatively, it is naturally also conceivable to guide the connecting section 14*c* from the first to the second side through a suitable passage opening in the piece of material 25.

Figure 4A:
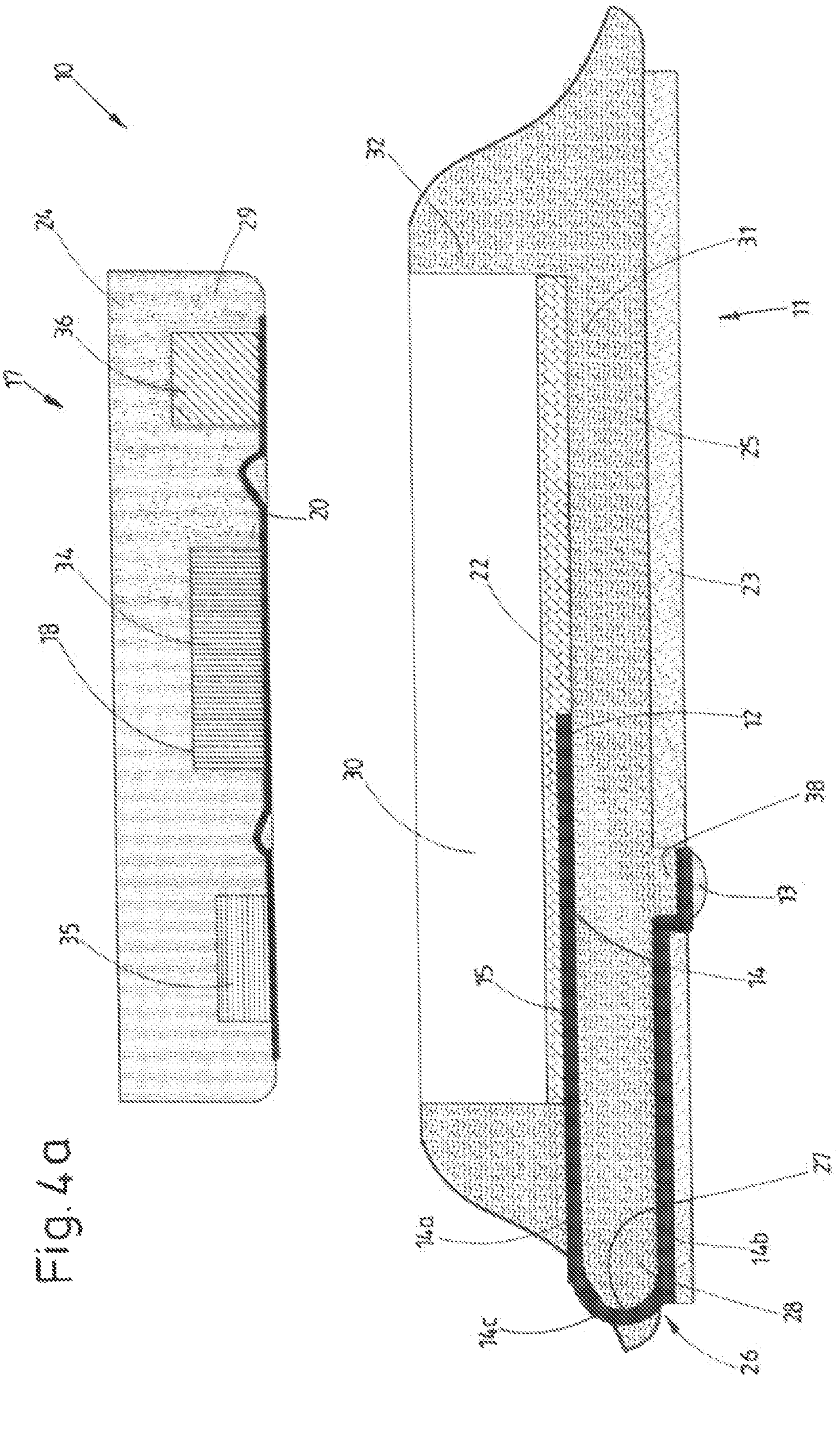
Figure 4B:
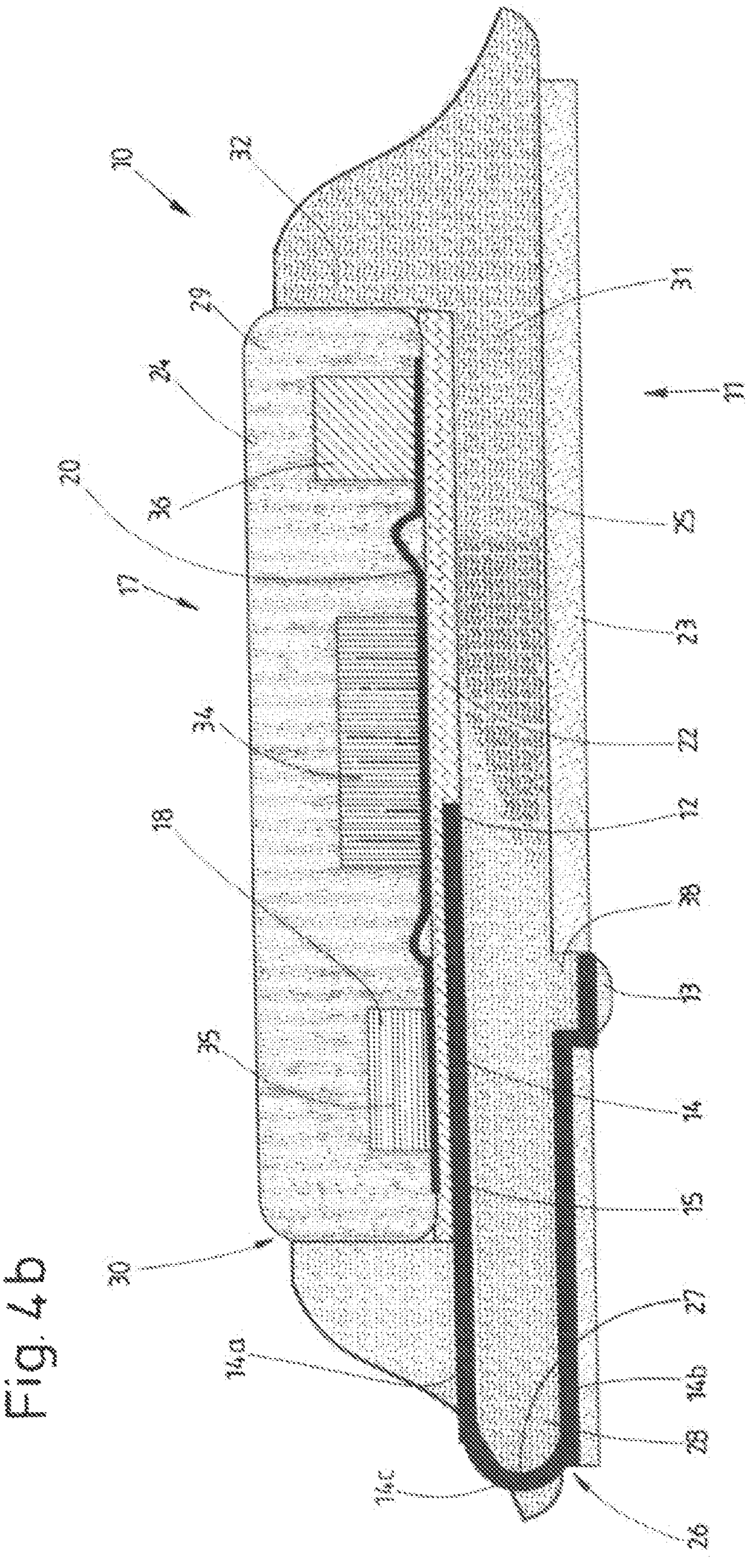

In the embodiment of FIGS. 4*a*, 4*b*, the protective envelope 24 of the electronics portion 17—similarly to the piece of material 25 of the sensor portion 11—is formed from a piece of material 29 of foam material made of plastic, for instance PU foam, or else from a silicone or an elastomer material. The electronics unit 18 is wholly or partly embedded into the piece of material 29.

Additionally introduced, for example by an embossing method, into the piece of material 25 of the sensor portion 11 is a depression 30 in which the electronics portion 17 rests and is held or secured there by the double-sided piece of adhesive material 22.

The depression 29 in the piece of material 25 of the sensor portion 11 may be bounded (in the downward direction) by a base wall 31 formed by the piece of material 25 and (to the side) by a side wall 32 which is connected in a one-piece manner to said base wall 31, is likewise formed by said piece of material 25 and laterally surrounds the depression 30.

As apparent, the electronics portion 17 or the piece of material 29 closes the depression 30 of the sensor portion 11 on an (otherwise open) side, namely on the (upper) side, which is opposite the side of the base wall 31 that faces the depression 30.

The piece of material 29 of the electronics portion 17 and the depression 30 are preferably matched to one another—though this is not absolutely necessary—in such a way that the piece of material 29 is force-fittingly bonded to the side wall 32 of the depression 30. This is done, for example, by introducing the piece of material 29 of the electronics portion 17 into the depression 30 with force-fitting contact with the side wall 32 and with lateral interference.

It is additionally apparent in FIGS. 4*a* and 4*b* that the outer face of the base wall 31 which is remote from the depression 30 has an elevation 38 that protrudes with respect to the adjoining flat plane of the outer face, on which there is disposed a/the measurement sensor 13, in order to improve the contact of the measurement sensor 13 with the body when the sensor unit 10 is disposed on the respective body.

Figure 5A:
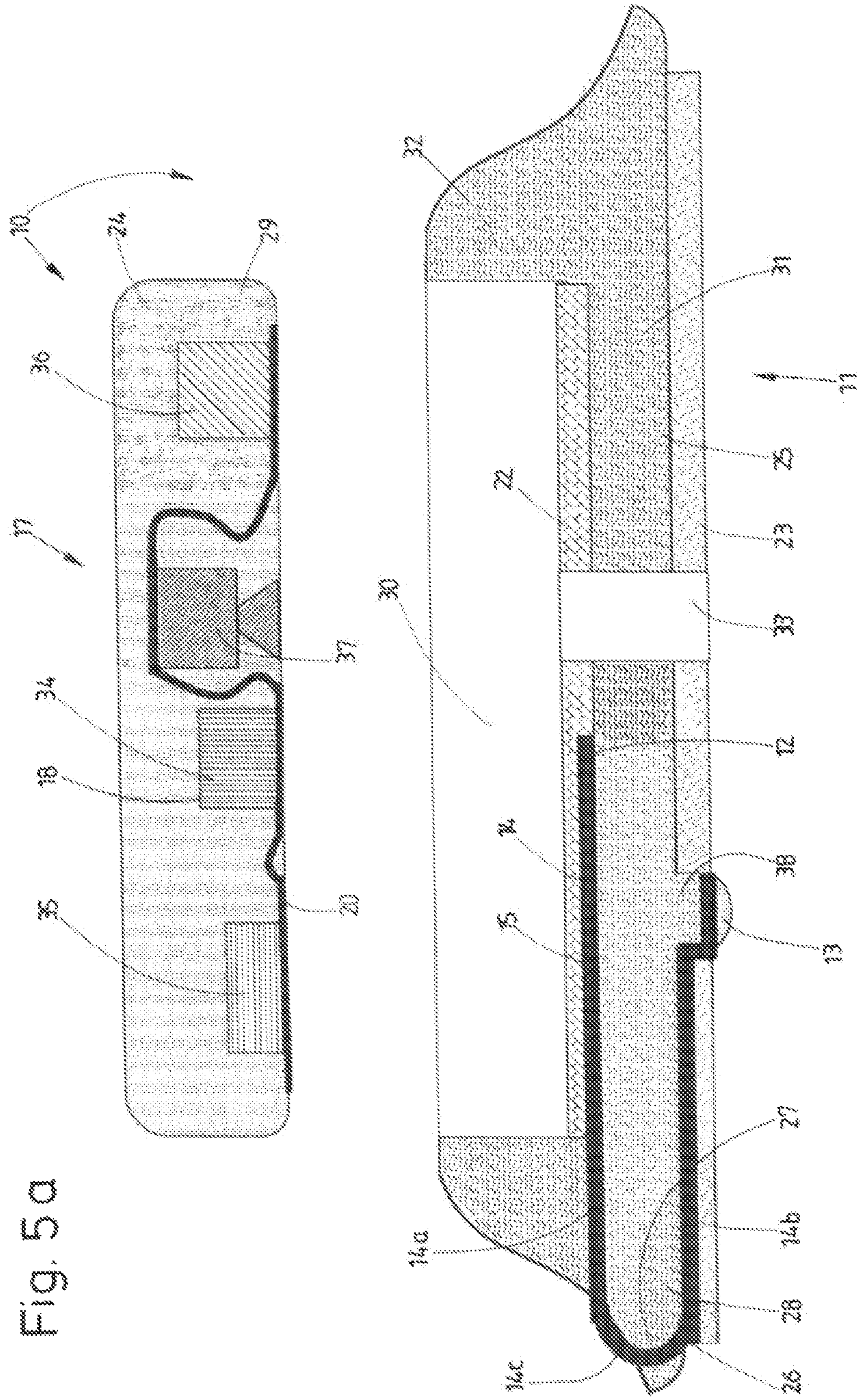
Figure 5B:
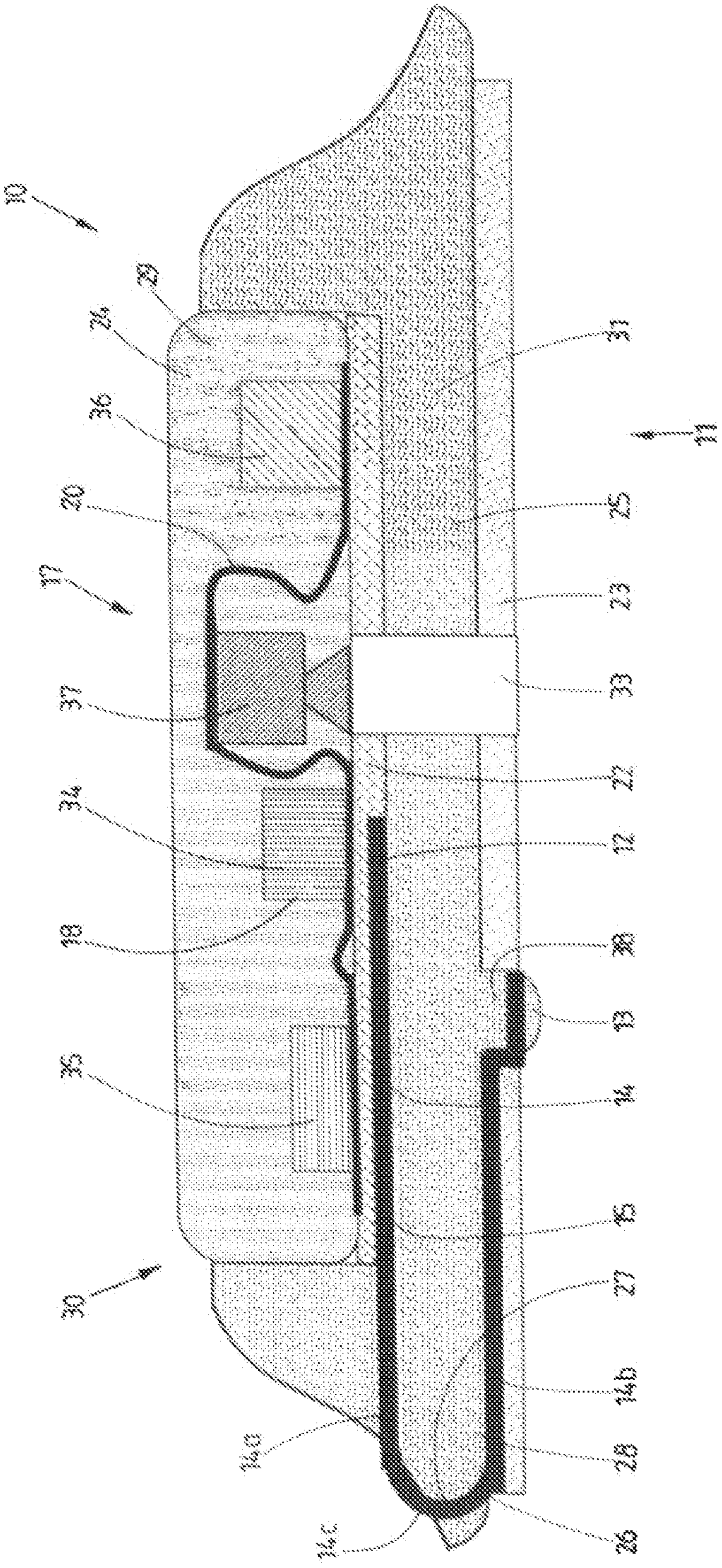

By comparison with the embodiment of FIGS. 4*a*, 4*b*, finally, the embodiment of FIGS. 5*a*, 5*b* has an electronic camera 37 assigned to the electronics portion 17. Specifically, this is positioned in the present case on the circuit board 20 of the electronics unit 18. This camera 37 can, for example, visually detect the skin of the body of the respective user.

Both the electronics portion 17 and the sensor portion 11 have an opening which together form a passage opening 33 through which the main viewing direction of the camera 33 is directed, and which extends up to the outer face of the sensor portion disposed on the body when the sensor unit 11 is used as intended.

Preferably, this passage opening 33 may be covered by a transparent protective layer or a corresponding transparent protective part which is especially disposed on the first and/or second side of the piece of material 25 of the sensor portion 11.

Figure 6:
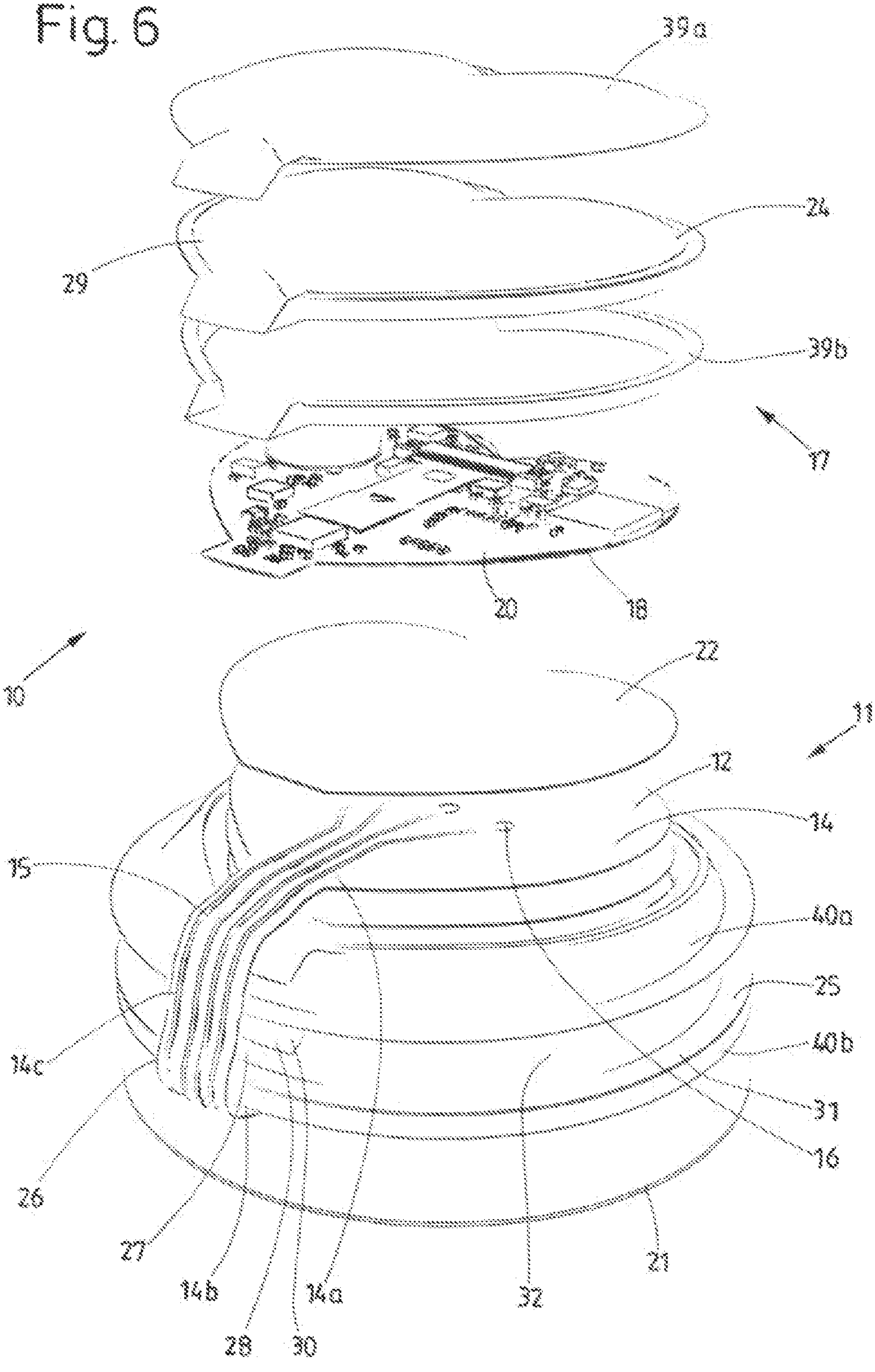

Only in FIG. 6 it is apparent that the piece of material 29 of the electronics portion 17 is provided with a (thin) film on each of the two opposite sides, namely on the side remote from the sensor portion 11 and on the side facing the sensor portion 11. This may, for example, be a TPU film.

In the same way, the piece of material 25 of the sensor portion 11 is also provided with such a film, namely the first and second sides of the piece of material 25, likewise especially with a TPU film.

PREFERRED EMBODIMENTS

1. A composite component comprising a piece of material (25) which is elastic in particular and is especially composed of a foam material or an elastomer material, where the piece of material (25) is bonded, inextricably in particular, to a film sensor (12) for measurement of one or more parameters, especially parameters of a human or animal body, having a piece of film (14) with at least one electrical wire disposed on said piece of film (14), and having at least one measurement sensor (13) which is preferably disposed on said piece of film (14) and is connected to the electrical wire in an electrically conductive manner.

2. The composite component according to embodiment 1, characterized in that the piece of film (14) of the film sensor (12) is bonded, in particular in a cohesive, inextricable or fixed manner, to the piece of material (25), especially to an outer face thereof, preferably by adhesive bonding, more preferably by means of a double-sidedly adhesive piece of adhesive material.

3. The composite component according to one or more of the preceding embodiments, characterized in that the foam material of the piece of material (25) is a polymer foam, especially a polyurethane foam.

4. The composite component according to embodiment 1, 2 or 3, characterized in that a first section of the piece of film (14) of the film sensor (12) is disposed on and is especially bonded (preferably inextricably) to a first side of the piece of material (25), and in that a second section of the piece of film (14) of the film sensor (12) is disposed on and especially bonded (preferably inextricably) to a second side of the piece of material (25) which is especially parallel to the first side at least in one region.

5. The composite component according to embodiment 4, characterized in that the two sections of the piece of film (14) are connected to one another, especially in a one-piece manner, by a connecting section of the piece of film (14), and said piece of film (14) is guided from the first side to the second side of the piece of material (25) to form a turnover region in which the connecting section is turned, especially by 180°, preferably in a u shape, about an edge of a preferably plate-shaped edge region of the piece of material (25).

6. The composite component according to embodiment 4 or 5, characterized in that the measurement sensor (13) is disposed on the second section of the piece of film (14) of the film sensor (12).

7. The composite component according to one or more of the preceding embodiments, characterized in that the electrical wire has been applied to an outer face of the piece of film (14) remote from the piece of material (25), especially by means of an additive printing method.

8. The composite component according to one or more of the preceding embodiments, at least according to embodiment 4, characterized in that an electrically insulating insulator material layer that covers the electrical wire on the outside is disposed on the second side of the piece of material (25), especially in contact with said second side.

9. The composite component according to embodiment 8, characterized in that the insulator material layer covers the entire second section of the piece of film (14) except for the measurement sensor(s) (13).

10. The composite component according to one or more of the preceding embodiments, characterized in that the piece of film (14), especially the first section of the piece of film (14) disposed on the first side of the piece of material (25), has one or more electrical contact elements for contacting of the film sensor (12).

11. The composite component according to one or more of the preceding embodiments, at least according to embodiment 4, characterized in that the measurement sensor (13) is disposed on the second side of the piece of material (25), especially on the second section of the piece of film (14).

12. The composite component according to one or more of the preceding embodiments, characterized in that the film sensor (12), especially the second section of the piece of film (14) of the film sensor (12) which is disposed on the second side of the piece of material (25), has one or more measurement sensors (13), namely at least one temperature sensor and/or one conductivity sensor and/or one pressure sensor and/or one impedance sensor.

13. The composite component according to one or more of the preceding embodiments, characterized in that the piece of material (25) has a passage opening that extends especially from the first side to the second side.

14. The composite component according to embodiment 13, characterized in that the passage opening is covered by a transparent protective layer disposed especially on the first and/or second side.

15. The composite component according to one or more of the preceding embodiments, characterized in that the second side of the piece of material (25) has one or more elevations (38) that protrude with respect to at least one other region, especially a flat region, of said second side, and in that the, more than one or each measurement sensor (13) is disposed on such an elevation (38).

16. The composite component according to one or more of the preceding embodiments, characterized in that the composite component is designed to interact with an electronics portion (17) which has an electronics unit for operating the film sensor (12) to form a sensor unit, and to be connected, especially releasably, to the electronics portion (17), especially with preferably releasable electrically conductive connection of the contact element(s) of the composite component to the electronics unit of the electronics portion (17).

17. The composite component according to one or more of the preceding embodiments, characterized in that the piece of material (25) has a depression (30) which has preferably been introduced by embossment and which is bounded by a base wall and by a side wall which is connected in a one-piece manner to said base wall and laterally surrounds the depression (30), especially by a depression (30) in which the electronics portion (17) of the sensor unit can be disposed.

18. The composite component according to one or more of the preceding embodiments, at least according to embodiment 4 or claim 17, characterized in that the depression (30) has been introduced into the first side of the piece of material (25), and in that the first section of the piece of film (14) of the film sensor (12) is disposed on the (inner) face of the base wall of the depression (30) that faces said depression (30).

19. The composite component according to embodiment 18, characterized in that the second section of the piece of film (14) of the film sensor (12) is disposed on an opposite side of the base wall from the side of the base wall that faces the depression (30).

20. A sensor unit comprising a composite component according to one or more of the preceding embodiments, and comprising an electronics portion (17) which is connectable, especially releasably, to the composite component and includes an electronics unit for operating the film sensor (12) of the composite component.

21. The sensor unit according to embodiment 20, further characterized by one or more features of embodiments 1-19.

LIST OF REFERENCE NUMERALS

10 sensor unit
11 sensor portion
12 film sensor
13 measurement sensor
14 piece of film
14*a* first section of piece of film
14*b* second section of piece of film
14*c* connecting section of piece of film
15 electrical wires
16 contact elements of film sensor
17 electronics portion
18 electronics unit
19 contact elements of electronics unit
20 circuit board
21 piece of adhesive material
22 electrically conductive piece of adhesive material
23 insulation layer
24 protective envelope
25 piece of material of sensor portion
26 turnover region
27 edge
28 edge region
29 piece of material of electronics portion
30 depression
31 base wall
32 side wall
33 passage opening
34 measurement electronics unit
35 transmission unit
36 energy supply unit
37 camera
38 elevation
39*a* film
39*b* film

40*a* film
40*b* film

The invention claimed is:

1. A composite component comprising a piece of material (25) which is elastic in particular and is composed of a foam material or an elastomer material or a silicone, where the piece of material (25) is bonded to a film sensor (12) for measurement of one or more parameters, having a piece of film (14) with at least one electrical wire disposed on said piece of film (14), and having at least one measurement sensor (13) which is disposed on said piece of film (14) and is connected to the electrical wire in an electrically conductive manner, wherein the piece of material (25) has a depression (30) which is bounded by a base wall and by a side wall which is connected in a one-piece manner to said base wall and laterally surrounds the depression (30) in which an electronics portion (17) of a sensor unit can be disposed.

2. The composite component as claimed in claim 1, wherein the piece of film (14) of the film sensor (12) is bonded in a cohesive, inextricable or fixed manner, to an outer face of the piece of material (25).

3. The composite component as claimed in claim 2, wherein the piece of film (14) of the film sensor (12) is bonded in a cohesive, inextricable or fixed manner, to an outer face of the piece of material (25) by adhesive bonding.

4. The composite component as claimed in claim 2, wherein the piece of film (14) of the film sensor (12) is bonded in a cohesive, inextricable or fixed manner, to an outer face of the piece of material (25) by means of a double-sidedly adhesive piece of adhesive material.

5. The composite component as claimed in claim 1, wherein the foam material of the piece of material (25) is a polymer foam.

6. The composite component as claimed in claim 5, wherein the foam material of the piece of material (25) is a polyurethane foam.

7. The composite component as claimed in claim 1, wherein a first section of the piece of film (14) of the film sensor (12) is disposed on and is bonded to a first side of the piece of material (25), and in that a second section of the piece of film (14) of the film sensor (12) is disposed on and bonded to a second side of the piece of material (25) which is parallel to the first side at least in one region.

8. The composite component as claimed in claim 7, wherein the two sections of the piece of film (14) are connected to one another in a one-piece manner, by a connecting section of the piece of film (14), and said piece of film (14) is guided from the first side to the second side of the piece of material (25) to form a turnover region in which the connecting section is turned about an edge of a plate-shaped edge region of the piece of material (25).

9. The composite component as claimed in claim 7, wherein an electrically insulating insulator material layer that covers the electrical wire on the outside is disposed on the second side of the piece of material (25) in contact with said second side.

10. The composite component as claimed in claim 7, wherein the measurement sensor (13) is disposed on the second side of the piece of material (25) on the second section of the piece of film (14).

11. The composite component as claimed in claim 7, wherein the second section of the piece of film (14) of the film sensor (12) which is disposed on the second side of the piece of material (25), has one or more measurement sensors (13).

12. The composite component as claimed in claim 11, wherein the one or more measurement sensors (13) are selected from the group consisting of a temperature sensor, a conductivity sensor, a pressure sensor, and an impedance sensor.

13. The composite component as claimed in claim 7, wherein the piece of material (25) has a passage opening that extends from the first side to the second side.

14. The composite component as claimed in claim 1, wherein the electrical wire has been applied to an outer face of the piece of film (14) remote from the piece of material (25) by means of an additive printing method.

15. The composite component as claimed in claim 1, wherein the composite component is designed to interact with an electronics portion (17) which has an electronics unit for operating the film sensor (12) to form a sensor unit, and to be releasably connected to the electronics portion (17); with a releasable electrically conductive connection of the contact element(s) of the composite component to the electronics unit of the electronics portion (17).

16. The composite component as claimed in claim 15, wherein the depression (30) has been introduced by embossment.

17. The composite component as claimed in claim 16, wherein the depression (30) has been introduced into the first side of the piece of material (25), and in that the first section of the piece of film (14) of the film sensor (12) is disposed on an inner face of the base wall of the depression (30) that faces said depression (30).

18. The composite component as claimed in claim 17, wherein the second section of the piece of film (14) of the film sensor (12) is disposed on an opposite side of the base wall from the side of the base wall that faces the depression (30).

19. A sensor unit comprising a composite component as claimed in claim 1, and further comprising an electronics portion (17) which is connectable, to the composite component and includes an electronics unit for operating the film sensor (12) of the composite component.

20. The sensor unit as claimed in claim 19, wherein the electronics portion (17) is releasably connectable to the composite component.

* * * * *